United States Patent [19]
Schaller et al.

[11] Patent Number: 5,777,602
[45] Date of Patent: Jul. 7, 1998

[54] OPERATING DEVICE FOR MEDICAL-TECHNICAL SYSTEM WORKPLACES

[75] Inventors: Günter Schaller; Tilo Endt, both of Freiburg; Michael Martin, Tuttlingen; Clemens Scholz, Freiburg, all of Germany

[73] Assignee: Huttinger Medizintechnik GmbH & Co., KG. Umkirch, Germany

[21] Appl. No.: 588,351

[22] Filed: Jan. 18, 1996

[30] Foreign Application Priority Data

Jan. 20, 1995 [DE] Germany ............... 195 01 581.9

[51] Int. Cl.⁶ .................................................. G09G 5/08
[52] U.S. Cl. ................................................ 345/157; 345/145
[58] Field of Search ................................. 345/156, 157,
345/184, 163; 434/45; 74/481, 512, 513,
514, 560, 471 XY; 433/72, 75; 606/10;
128/661.03

[56] References Cited

U.S. PATENT DOCUMENTS

| 3,809,454 | 5/1974 | Brambring . | |
|---|---|---|---|
| 5,098,426 | 3/1992 | Sklar et al. . | |
| 5,126,723 | 6/1992 | Long et al. . | |
| 5,148,152 | 9/1992 | Stueckle et al. | 345/156 |
| 5,230,623 | 7/1993 | Guthrie et al. | 345/163 |
| 5,245,320 | 9/1993 | Bouton | 345/167 |
| 5,334,997 | 8/1994 | Scallon | 345/167 |
| 5,552,807 | 9/1996 | Hayes | 345/156 |

FOREIGN PATENT DOCUMENTS

| 0 330 270 | 8/1989 | European Pat. Off. . | |
|---|---|---|---|
| 0 571 827 A1 | 12/1993 | European Pat. Off. . | |
| 3873776 | 3/1993 | Germany | A61C 19/00 |
| 91 12 052.7 | 3/1993 | Germany . | |
| 43 21 934 A1 | 1/1994 | Germany . | |
| 92 18 373.5 | 3/1994 | Germany . | |
| 43 10 842 A1 | 10/1994 | Germany . | |
| 2 251 774 | 7/1992 | United Kingdom . | |
| WO 93/22232 | 11/1993 | WIPO . | |

OTHER PUBLICATIONS

JP 61-18028 A., In: Patents Abstracts of Japan, P-467, Jun. 12, 1986, vol. 10, No. 165.

*Primary Examiner*—Xiao Wu
*Attorney, Agent, or Firm*—Antonelli, Terry, Stout & Kraus, LLP

[57] ABSTRACT

The invention is related to an operating device for apparatus combinations of medical-technical system workplaces, especially for the minimal invasive surgery. The individual apparatus of the apparatus combination are connected to a computer (28) having a monitor (30) and driven by way of foot-actuated actuating members. In order to improve the usability and flexibility, an actuating member fashioned to be a foot roller (56) provides computer compatible signals, while at least one further actuating member is formed to be a foot switch (58,60) and can be assigned to one of the apparatus-specific functional elements software-controlled by the actuation of the foot roller (56). A switch assignment field (88,90) assigned to the foot switch (58,60) for the symbolic display of the functional element assigned to the foot switch (58,60) at that time is provided on the monitor (30).

22 Claims, 6 Drawing Sheets

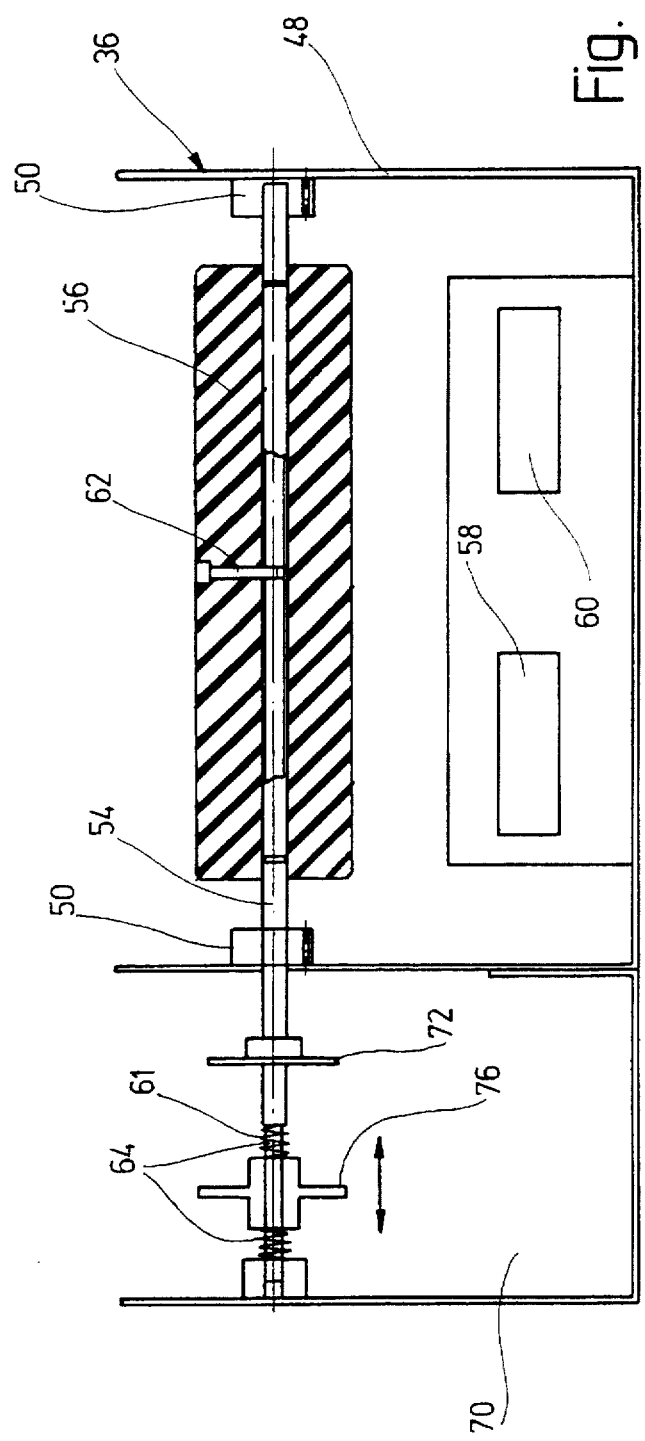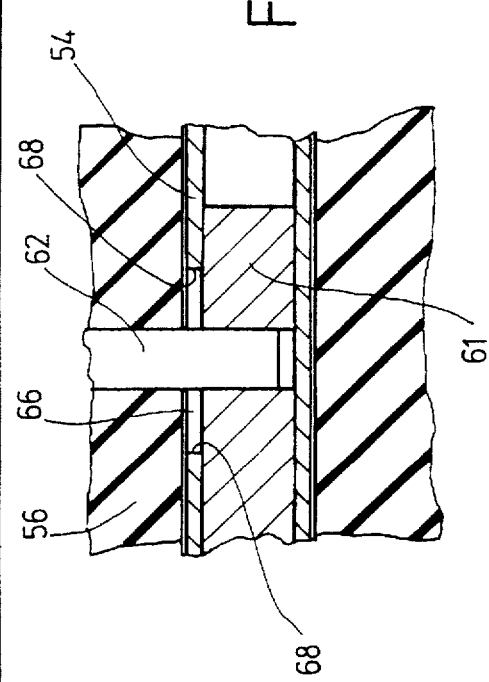

INSUFFLATION
PRESS. RELEASE
FREEZE
VIEW
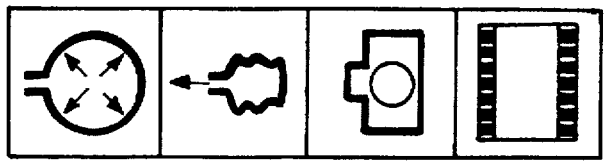
CUT MONOP.
COAG. MONOP.
CUT BIPOLAR
COAG. BIPOLAR
SUCTION
IRRIGATION
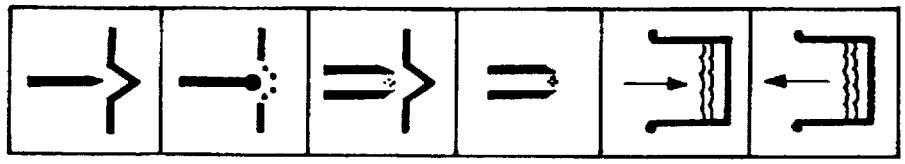
Fig. 5

OPERATING DEVICE FOR MEDICAL-TECHNICAL SYSTEM WORKPLACES

BACKGROUND OF THE INVENTION

1. Field of the Invention

The invention relates to an operating device for apparatus combinations of medical-technical system workplaces, especially for open or minimal invasive surgery, comprising at least one computer which is connected to individual apparatus of the apparatus combination, a monitor, and an actuating structure provided for driving apparatus-specific functional elements and having a plurality of foot-actuatable actuating members.

2. Description of the Prior Art

In modern surgery medical-technical system workplaces a plurality of apparatus of different functions are simultaneously used. In the past, the antiseptically prepared surgeon could control the operation of the apparatus only by oral orders to auxiliary medical personnel. Misinterpretations of the orders and erroneous operation of the apparatus cannot always be avoided, especially if the personnel is inexperienced and unmotivated. Newly acquired and often complicated apparatus in the minimal invasive surgery field further complicate this situation.

An improvement in this respect has already been achieved by the use of foot switches, by the use of which the surgeon can drive individual, predetermined functional elements of the apparatus combination. Even so, assigning new tasks to the actuating members is possible only by the use of additional operating elements which are not actuatable by foot.

SUMMARY OF THE INVENTION

It is the object of the present invention to provide an operating device of the type described above, which permits the surgeon to dependably operate even complicated system workplaces having a plurality of apparatus-specific functional elements exclusively by foot-actuation without the help of auxiliary personnel.

The solution according to the invention is based on the foot-actuated actuating structure serving to drive apparatus-specific functional elements as well as being formed as an input device for the computer for transmitting computer-compatible control signals. The computer comprises program routines which are alternatively selectable by way of the actuating structure and are used for configuring selected functional elements, for alternatively assigning individual actuating members to configured functional elements, and for driving the functional elements by way of their assigned actuating members. To this end, the individual functional elements are connected to the computer by way of a bus system.

The configuration is realized by assembling the required functional elements as well as by their parameterizing for a specific use.

The measures according to the invention enable the surgeon to work effectively using the available functional elements as well as possible, without the need of assistance. If the need arises, the required functional elements may at any time be newly configured or parameterized, arbitrarily assigned to the individual actuating members, and driven by these. During this, the hands of surgeon remain free for working in the antiseptic region.

On the other hand, in this type of multifunctional assignment of actuating members the simplicity of operation and the comprehensibility of the chosen setting should not be lost. In order to achieve this, according to an advantageous embodiment of the invention the actuating structure further comprises at least two foot switches and a foot roller which can be rotated as well as axially displaced. The operating device should preferably have at least one digitizing device which is coupled to one of the actuating members and which serves to generate computer-compatible output signals. The digitizing device coupled to the foot roller serves, for instance, for the software-supported motion control of a cursor on the monitor. To this end, an incremental transducer, which is dependent on the angle and direction of rotation, is advantageously connected to the roller in a non-rotatable manner. The incremental transducer may for instance comprise a two-track holed or slotted disk which is scanned by way of a fork-type light barrier or a toothed roller which is made of a magnetizable material and which can be scanned inductively.

In order to be able to implement two-dimensional cursor movements on the monitor using the foot roller, two switching members which are actuatable in both directions by an axial movement of the foot roller and which serve to transmit computer-compatible control signals are additionally provided according to the invention. In this, the switching members which are actuatable by the axial movement of the foot roller may be connected to a switching structure for triggering a single switching impulse or a time-delayed series of switching impulses when the actuation is continuous (auto repeat function). The switching members may be formed to be limit switches, proximity switches or analog or digital path-measuring systems having a potentiometer function. In order to avoid errors in the axial actuation of the foot roller, the foot roller may be provided with lateral roller flange disks.

In a prefered constructive embodiment of the operating device, the foot roller is positioned on a hollow shaft in a non-rotatable and axially moveable manner, the hollow shaft being borne on a pedestal in a manner which permits rotation about a horizontal axis and carrying the incremental transducer of the digitizing device, and inside of which a push rod which is rigidly coupled to the foot roller is positioned, the push rod being axially moveable and spring-centered, and bearing an actuating element, preferably formed to be a reflector disk, for the switching members. In order to avoid contamination, the foot roller and/or the push rod are sealed with respect to the hollow shaft in a fluid-tight manner.

In order to increase the clarity of the display one switch assignment window which is assigned to each of the foot switches is provided on the monitor for the symbolic display of the functional element assigned to the foot switches at that time.

The reassignment of the foot switches may be performed simply and quickly if a function field is assigned to each apparatus-specific function element within a menu window alternatively displayed on the monitor, the menu window preferably being a scroll-down menu, and if the function fields are driveable by the cursor on the monitor by way of actuating the foot roller and selectable by actuating the affiliated foot switch, whereby the corresponding function symbol is transposed into the switch assignment window, so that a functional connection is established between the foot switch and the functional element symbolically displayed in the switch assignment window. It is of advantage when a symbol field which may be displayed together with the menu window is provided on the monitor for displaying the function symbol of the function element which is selected in the menu window at that time and which is to be transposed into the switch assignment field during the selection. For the selection of the program routines the foot switches or a pair of foot switches or the switching members which are actuatable by the axial movement may for instance be actuated within a predetermined small time interval. A similar effect may be achieved when two of the foot switches are actuated synchroneously in a predetermined time interval. In this manner the connection between a foot switch and the affiliated functional element may be created or acknowledged.

In order to increase the clarity of the display and to improve the control of important data during the surgery, a status window for permanently displaying selectable operational and patient data is provided on the monitor.

Especially during endoscopic surgery and laparoscopic surgery it is imperative to provide an image window for video images on the monitor, wherein a cursor which is controlled by the foot roller should be moveable in the image window in two dimensions. Of course the image window is also suited to view images from the central computer which were previously stored for the purpose of documentation or of images from an external storage medium.

In order to be able to continue or finish undergoing surgery during a computer malfunction or a power failure, a safety circuit is provided which switches the foot switches and/or the foot roller through to the predetermined, apparatus-specific function elements during the computer malfunction or power failure.

BRIEF DESCRIPTION OF THE DRAWINGS

In the following, the invention is further described with the aid of embodiments schematically shown in the drawing.

FIG. 3a shows a front view of the foot-actuation element according to FIG. 2;

FIG. 3b shows a front view of the foot-actuation element according to FIG. 2;

FIG. 5 shows the assignment of the symbols to the functional elements.

DESCRIPTION OF THE PREFERRED EMBODIMENTS

Figure 1:
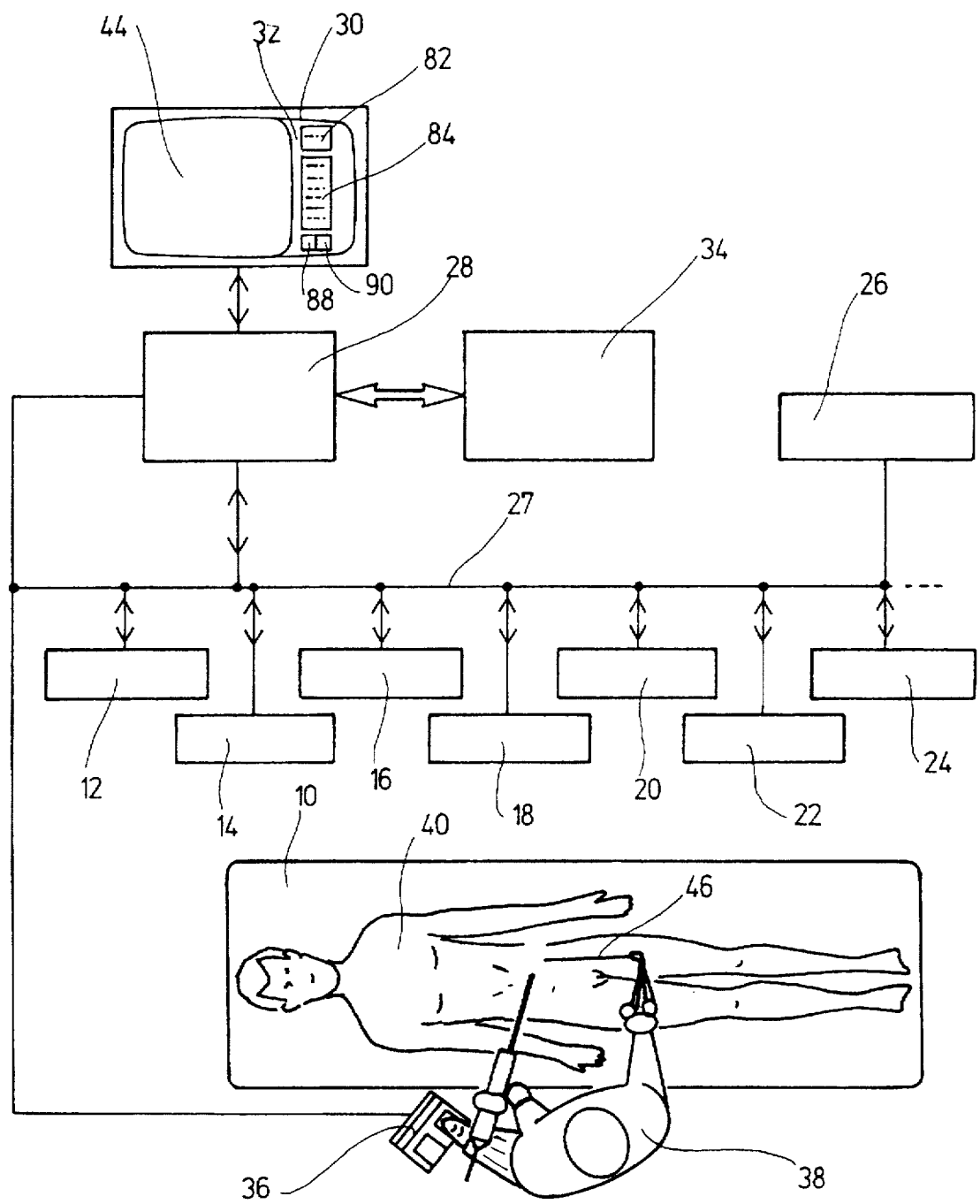
FIG. 1 shows a schematic view of a system workplace for minimal invasive surgery.

The systematic workplace schematically shown in FIG. 1 is located in an operating room having an operating table 10 and is intended to be used in minimal invasive surgery. The technique of minimal invasive surgery is used primarily in abdominal and thorax surgery, gynecology and urology. The systematic workplace comprises a collection of apparatus having a plurality of instruments, such as a laser surgery instrument 12, a HF-surgery apparatus 14, a cold light source 16, an irrigation and suction pump 13, an insufflator 20, an ultrasonic measuring device 22, a diagnosis device 24, and a camera control device 26. The apparatus 12 to 26 are connected to an input-output port of a computer 28 by way of a bus-system 27, a monitor 30 having a screen 32 additionally being connected to the computer, which further makes data exchange with an external data archive 34 possible.

The actuation of the apparatus 12 to 26 and of the data exchange with the data archive 34 is softwarecontrolled by way of a foot-actuated operational control 36 through the bus system 27 common to all the apparatus. The operational control element 36 is se t up on the floor in the immediate vicinity of the operating table 10 and is foot-actuated by the surgeon 38. In laparoscopic surgery the operation is performed using an elongated instrument 46 inserted into the abdominal cavity through a metallic sheath. The operation site in the patient 40 is viewed using a video camera and an endoscope 42 and transmitted to an image window 44 of the screen 32 by way of the camera control device 26. The necessary illumination of the operation site is done by the cold light source 16 which is connected to the endoscope 42.

Figure 2:
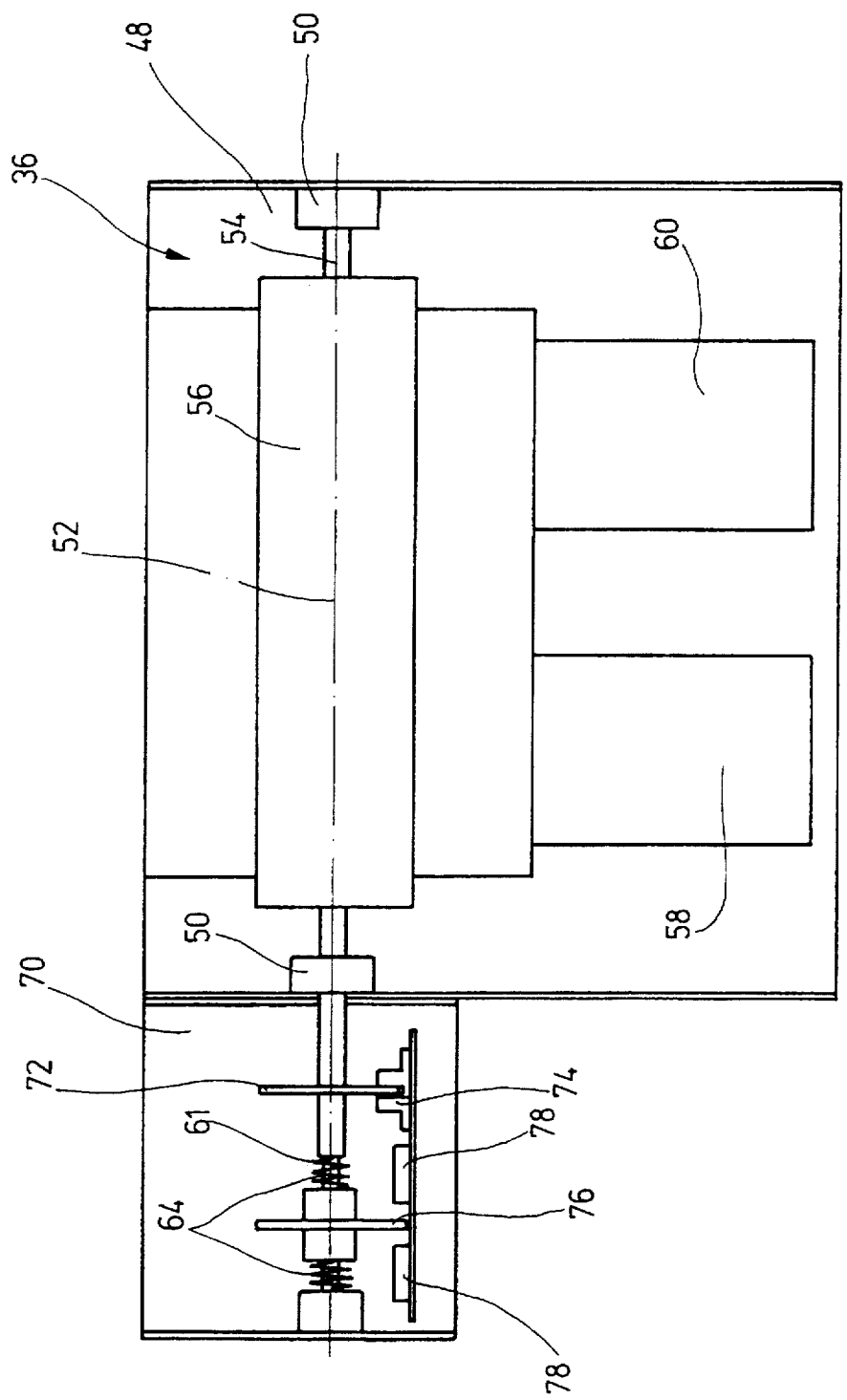
FIG. 2 shows a top view of the foot-actuation element according to FIG. 1.

As can be seen from FIGS. 2 and 3, the operational control 36 consists mainly of a foot roller 56 rotatably supported on a horizontal axis 52 on the pedestal 48 and two foot switches 58, 60 positioned next to each other on the pedestal. The foot roller 56 is disposed in a non-rotatable and axially moveable manner on a hollow shaft 54 which in turn is rotatably support by bearings 50 of the pedestal 48. Located inside the hollow shaft 54 is an axially moveable push rod 61, which is rigidly couplable to the foot roller 56 by way of a bolt 62 and which is held in a springcentered center position by two springs 64 in its neutral state. The bolt 62 extends radially through a slot 66 in the hollow shaft 54, wherein the ends of the slot 66 form limit stops 68 for the guide roller 56 and the push rod 61 during the axial movement with respect to the hollow shaft 54 in both directions. An increment disk 72 having slit-like openings (not shown) is positioned on the end of the hollow shaft 54 extending into the casing part 70 of the pedestal 48, the slit-like openings of the increment disk 72 forming together with the fork-type light barrier, which is rigidly mounted on the pedestal, an incremental transducer for the angle and direction of rotation of the foot roller 56. A plate-like reflecting disk 76 is disposed on the push rod 61, the reflecting disk cooperating together with the two reflecting-type light barriers 78 and an analyzing circuit in the sense of a proximity switch for the left and right movement of the foot roller 56.

The two foot-switches 58, 60 are preferably formed to be push buttons, which close an electric circuit when pushed down against the force of a spring and which are therefore suited to execute electric switching functions. Their distance from one another is chosen such that they may also be actuated mutually by one foot.

The incremental transducer 72, 74 responding to the rotation of the foot roller 56 is used for the one dimensional (vertical) motion control of a cursor 80 on the monitor screen 32, while the proximity switches 76, 78 which are activated by the axial movement of the foot roller 56 are used for the step-wise lateral movement of the cursor 80, if need be incorporating an auto-repeat function.

As can be seen from FIG. 1, the screen is subdivided during the operation of the systematic workplace into an image window 44, a permanently displayed status window 82 for the display of important apparatus and patient data, a menu window 84 having a scroll menu 86 driven by the foot roller, and a symbol field 87 as well as two permanently displayed switch assignment fields 88, 90 which are assigned to the two foot switches 58, 60.

The screens schematically shown in FIGS. 4a to f illustrate how a reassignment of the foot switches 58, 60 is performed with the aid of the foot roller 56.

Initially the menu is called up by a corresponding program routine, for instance by the simultaneous actuation of the two foot switches 58, 60, and displayed on the screen 32.

Figure 4C:
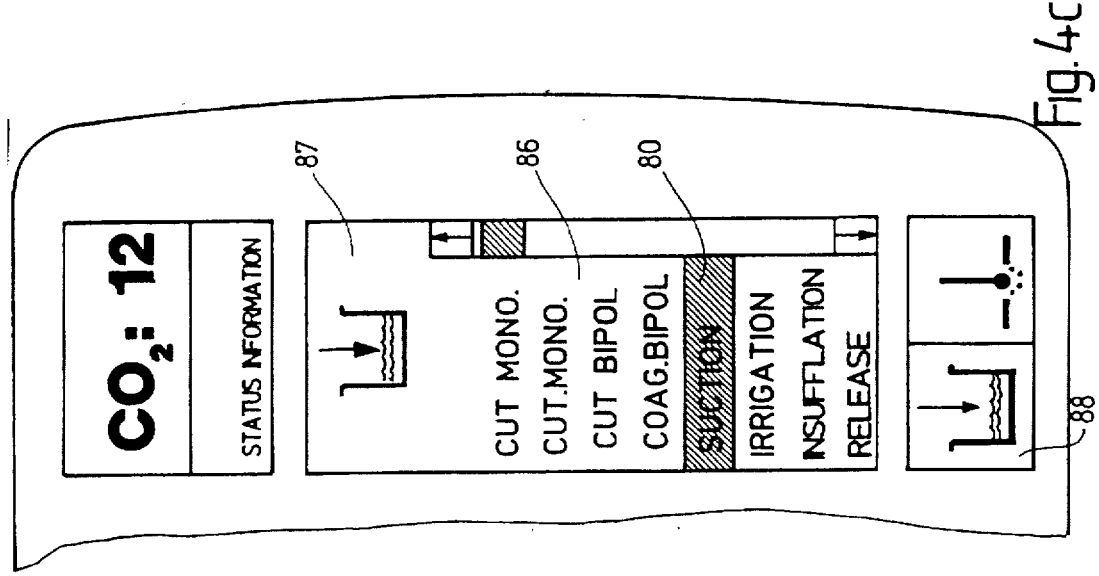
FIG. 4a to f show details of the monitor including the status window, the menu window and the switch assignment field.
Figure 4B:
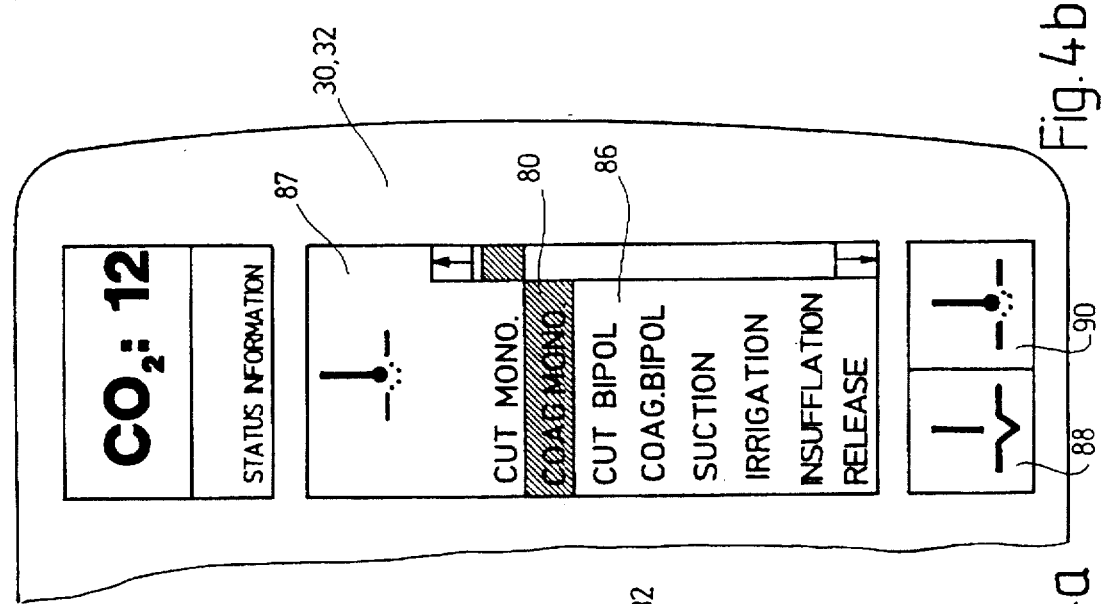
Figure 4A:
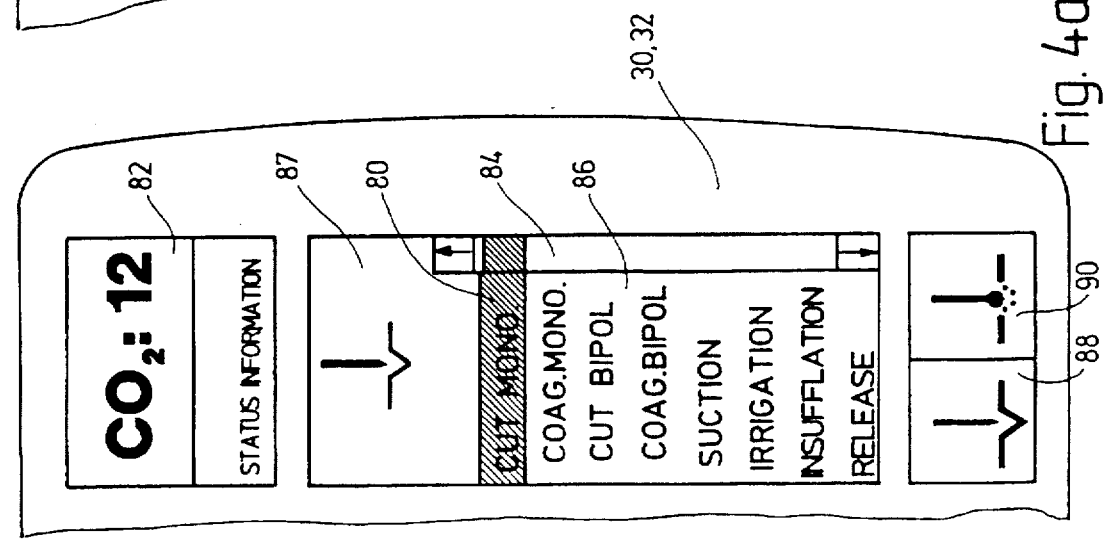
Figure 4F:
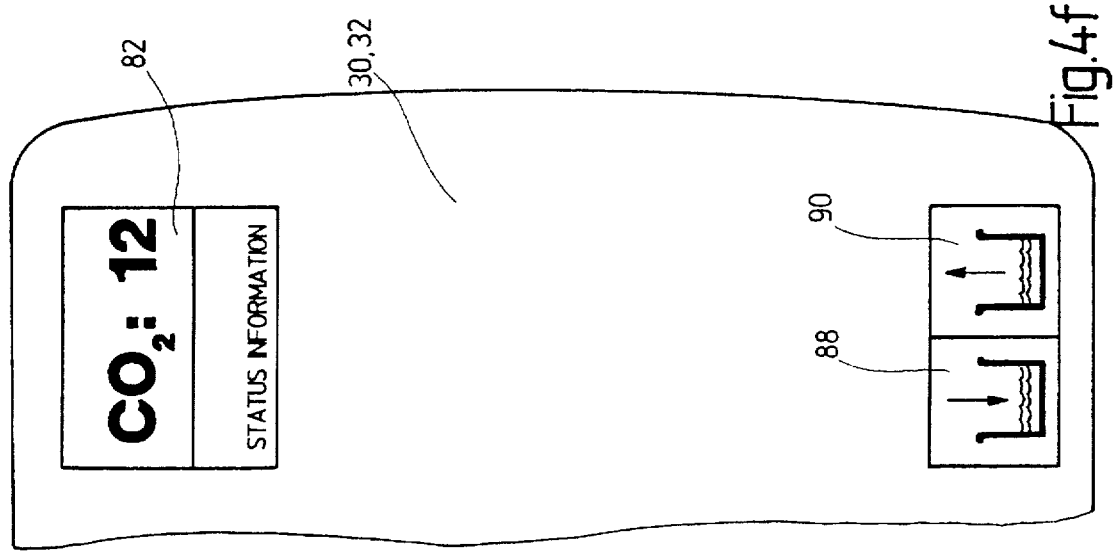
Figure 4E:
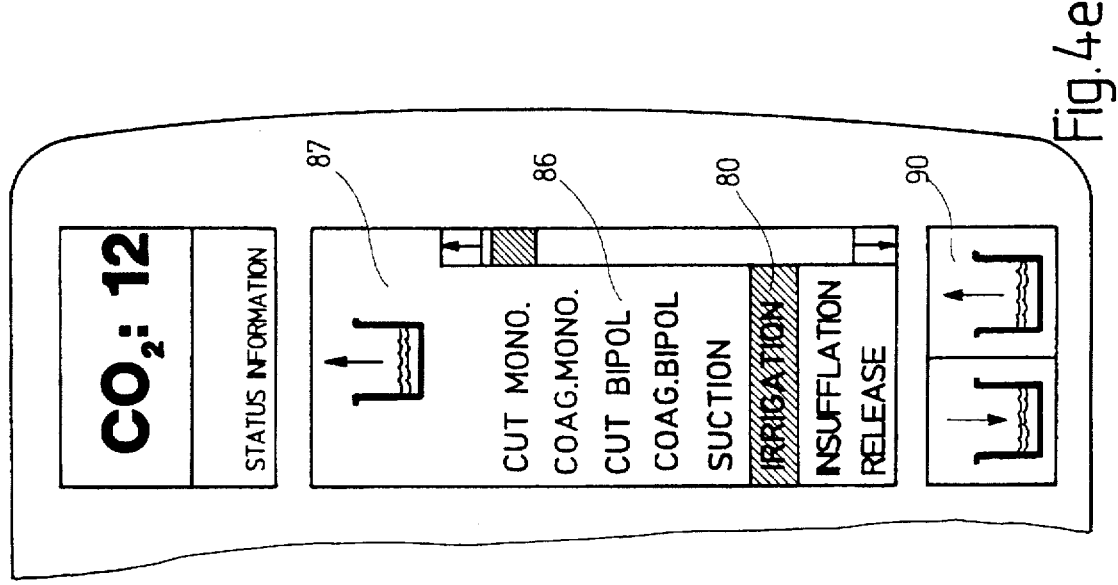
Figure 4D:
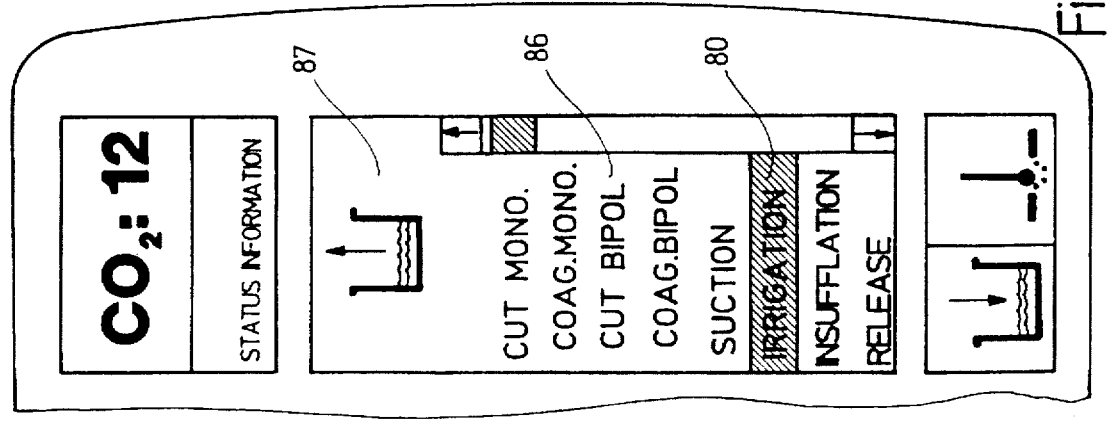

The momentary switch assignment is depicted by the symbols in the switch assignment fields 88, 90. As a comparison with FIG. 5 shows, the functions momentarily assigned to the foot switches 58, 60 are "CUT MONO" (monopolar cutting) on the one hand and "COAG.MONO" (monopolar coagulation) on the other hand. The cursor bar 80 is located in the menu field "CUT MONO" (monopolar cutting), so that the corresponding symbol is displayed in the symbol field 87. When scrolling through the menu 86, the functional symbol displayed in the symbol field 87 changes in the sense of the assignment according to FIG. 5. In order to reprogram the left foot switch 58 to correspond to the functional element "SUCTION", first the menu field shown in FIG. 4c is chosen and the corresponding symbol is then taken over from the symbol field 87 into the switch assigment window 88 by pushing down on the left foot switch 58. If additionally the foot switch 60 is to be assigned to the functional element "IRRIGATION", the menu field in question is elected (FIG. 4d and e) and the corresponding symbol is taken over from the symbol field 87 into the right switch window 90. For the final programming both foot switches 58, 60 are actuated together in a predetermined time interval of maximal 300 ms. The establishment of the functional connection is indicated by the disappearance of the menu window 84 (FIG. 4f).

Apart from the functions shown in the scroll down menu according to FIGS. 4a to e, the images from the image window 44 can be recorded (freeze) or recalled from the memory and displayed in the image window 44 (view) by way of the scroll down menue (cf. FIG. 5).

In order to be able to finish an undergoing surgery in the case of a computer malfunctions there is provided a safety circuit (not shown) which ensures that in such a case the foot switches 58, 60 are each switched to one predetermined functional element independent from the software.

In summary, the following can be stated: The invention is related to an operating device for apparatus combinations of medical-technical system workplaces, especially for the minimal invasive surgery. The individual apparatus of the apparatus combination are connected to a computer 28 having a monitor 30 and driven by way of foot-actuated actuating members. In order to improve the usability and flexibility, an actuating member fashioned to be a foot roller 56 provides computer compatible signals, while at least one further actuating member is formed to be a foot switch 58, 60 and can be assigned to one of the apparatus-specific functional elements software controlled by the actuation of the foot roller 56. A switch assignment field 88, 90 assigned to the foot switch 58, 60 for the symbolic display of the functional element assigned to the foot switch 58, 60 at that time is provided on the monitor 30.

We claim:

1. An operating device for apparatus combinations of medical-technical system workplaces, for use with open or minimal invasive surgery, comprising:

at least one computer which is connected to individual apparatus-specific functional elements of the apparatus combinations, a monitor coupled to the at least one computer; and an actuating structure, coupled to the computer, for driving the apparatus-specific functional elements and having a plurality of foot-actuatable actuating members;

the at least one computer is coupled to the apparatus-specific functional elements by a bus-system; and the at least one computer comprises program routines which are alternatively selectable by way of the actuating structure and are used for configuring selected individual apparatus-specific functional elements, for alternatively assigning individual actuating members to configured apparatus-specific functional elements, and for driving the apparatus-specific functional elements by way of their assigned actuating members.

2. The operating device of claim 1, wherein the actuating structure further comprises at least two foot-switches and a foot-roller which can be rotated as well as axially displaced.

3. The operating device of claim 1, wherein the actuating structure further comprises at least one digitizing device which is coupled to one of the actuating members and serves to generate computer-compatible output signals, for software-supported motion control of a cursor on the monitor.

4. The operating device of claim 2, wherein an incremental transducers, which is dependent on the angle and direction of rotation, is connected to the foot roller in a non-rotatable manner.

5. The operating device of claim 4, wherein the incremental transducer comprises a two-track holed or slotted disk which is scanned by way of a fork-type light barrier.

6. The operating device of claim 4, wherein the incremental transducer comprises a toothed roller which is made of a magnetizable material and which can be scanned inductively.

7. The operating device of claim 2, further comprising two switching members which are actuatable in both directions by an axial movement of the foot roller and which serve to transmit computer-compatible control signals, for software-supported motion control of a cursor on the monitor.

8. The operating device of claim 7, wherein the switching members, which are actuatable by the axial movement of the foot roller, are limit switches, proximity switches or analog or digital path-measuring systems.

9. The operating device of claim 7, wherein the two switching members, which are actuatable by the axial movement of the foot roller, are connected to a switching structure for triggering a single switching impulse or a time-delayed series of switching impulses when actuation is continuous.

10. The operating device of claim 7, wherein the switching members, which are proximity switches, comprise a reflecting-type light barrier and a reflector which is moveable by way of the foot roller.

11. The operating device of claim 7, wherein the foot roller has lateral roller flange disks.

12. The operating device of claim 7, wherein the foot roller is positioned on a hollow shaft in a non-rotatable and axially moveable manner, the hollow shaft is on a pedestal which permits rotation about a horizontal axis and carries the incremental transducer of a digitizing device, and in which a push rod, which is rigidly coupled to the foot roller, is positioned, the push-rod being axially moveable and spring-centered, and bearing an actuating element which is a reflector, for the switching members.

13. The operating device of claim 12, wherein the foot roller and/or the push rod are sealed with respect to the hollow shaft in a fluid-tight manner.

14. The operating device of claim 2, wherein the program routines are selectable by a double-click of one of the foot switches and/or by an axial actuation of the foot roller within a predetermined time interval.

15. The operating device of claim 2, wherein two of the actuating members, which are formed to be foot switches, are actuable synchronously in a predetermined time interval, for creating a connection between the foot switches and the functional element.

16. The operating device of claim 15, wherein a further computer command is selectable by a synchronous double-actuation of the pair of foot switches.

17. The operating device of claim 2, wherein one switch assignment window, which is assigned to each of the foot switches, is provided on the monitor for the symbolic display of an apparatus-specific functional element assigned to the foot switches at that time.

18. The operating device of claim 2, wherein a function field is assigned to each apparatus-specific function element within a menu window alternatively displayed on the monitor, the menu window being a scroll-down menu, and wherein each function field is driveable by the cursor on the monitor by way of actuating the foot roller and selectable by actuating affiliated foot switches, whereby the corresponding function symbol is transposed into the switch assignment window, so that a functional connection is established between the foot switch and the apparatus-specific functional element symbolically displayed in the switch assignment window.

19. The operating device of claim 18, wherein a symbol field, which is displayable together with the menu window, is provided on the monitor for displaying the function symbol of the apparatus-specific function element, which is selected in the menu window at a time of displaying the function symbol and which is transposed into the switch assignment field during being selected.

20. The operating device of claim 1, wherein a status window, for permanently displaying selectable operational and patient data, is provided on the monitor.

21. The operating device of claim 7, wherein an image window for video images is provided on the monitor, and wherein a cursor, which is controlled by the foot roller, is moveable in the image window in two dimensions.

22. The operating device of claim 2, wherein the foot switches and/or the foot roller are switched through to the predetermined function elements by way of a safety circuit independent of the software and bus.

* * * * *